United States Patent [19]

Laine

[11] Patent Number: 5,440,011

[45] Date of Patent: Aug. 8, 1995

[54] ION CONDUCTING POLYMERS

[75] Inventor: Richard M. Laine, Ann Arbor, Mich.

[73] Assignee: Washington Research Foundation, Seattle, Wash.

[21] Appl. No.: 336,561

[22] Filed: Nov. 9, 1994

Related U.S. Application Data

[63] Continuation of Ser. No. 27,120, Mar. 4, 1993, abandoned, which is a continuation-in-part of Ser. No. 792,214, Nov. 12, 1991, Pat. No. 5,216,155, which is a continuation-in-part of Ser. No. 509,022, Apr. 13, 1990, Pat. No. 5,099,052.

[51] Int. Cl.$^6$ .................................. C08G 65/34
[52] U.S. Cl. .................................. 528/425; 556/443; 556/464; 556/482; 556/405; 544/229
[58] Field of Search ............... 556/443, 464, 482, 405; 544/229; 528/425

[56] References Cited

U.S. PATENT DOCUMENTS

| | | | |
|---|---|---|---|
| 3,455,980 | 7/1969 | Frye | 260/448.8 |
| 4,447,628 | 5/1984 | Farnham | 556/415 |
| 4,577,003 | 3/1986 | Farnham | 556/464 |
| 4,617,413 | 10/1986 | Corriu et al. | 556/464 |
| 4,632,967 | 12/1986 | Farnham | 526/194 |
| 4,841,084 | 6/1989 | Corriu et al. | 556/464 |
| 5,099,052 | 3/1992 | Laine | 556/443 |

FOREIGN PATENT DOCUMENTS 0191259  8/1986  France .
WO91/16328 10/1991  WIPO .

OTHER PUBLICATIONS

Youndahl, K. A. et al., "Synthesis of Soluble Siliconates and Siloxanes from Silica" (abstract No. 421), Spring Newsletter, Jan. 1989, Division of Inorganic Chemistry, American Chemical Society.

Holmes, R. R. et al., "Cyclic Pentaoxy Siliconates," Phosphorus, Sulfur, and Silicon 42:1–13, 1989.

Boudin, A. et al., "Reaction of Grignard Reagents with Dianionic Hexacoordinated Silicon Complexes: Organosilicon Compounds from Silica Gel," Angew. Chem. Int. Ed. Engl. 25(5):474–475, 1986.

O3 above in Herman.

Barnum, D. W., "Reactions of Catechol with Colloidal Silica and Silicic Acid in Aqueous Ammonium," Inorganic Chemistry 11(6):1424–1429, 1972.

Perozzi, E. F. et al., "Facile Synthesis of Isolable Organic Derivatives of Hypervalent Sulfer, Phosphorus, and Silicon. Introduction of a Stabilizing Bidentate Ligand via Its Dilithio Derivative," J. Am. Chem. Soc. 101(6):1591–1593, 1979.

Farnham, W. B. et al., "Stereomutation at Pentacoordinate Silicon by Intramolecular Ligand Exchange," J. Am. Chem. Soc. 103:4608–4610, 1981.

Frye, C. L., "Pentacoordinate Silicon Derivatives. IV. Aklylammonium Siliconate Salts Derived from Aliphatic 1,2–Diols," J. Am. Chem. Soc. 92(5):1205–1210, 1970.

Frye, C. L. et al., "Pentacoordinate Silicon Compounds. V. Novel Silatrane Chemistry," J. Am. Chem. Soc. 93(25):6805–6811, 1971.

Laine, R. M. et al., "Synthesis of pentacoordinate silicon complexes from $SiO_2$," Nature 353:642–644, 1991.

Kopylov, V. M. et al., "Transesterification of tetraethoxysilane with bi-functional alcohols in presence of nucleophilic catalysts," J. Gen. Chem. USSR 57:2086–2088, 1988 (translation of Zhurnal Obshchei Khimii 57:2333–2336, 1987).

Youngdahl Blohowiak, K. A. et al., "Synthesis of Penta-alkoxy-and Penta-aryloxy Silicates Directly from $SiO_2$," In Inorganic and Organometallic Polymers with Special Properties, Laine, R. M. (Ed.); Kluwer Academic Publishers, The Netherlands, pp. 99–111, 1992.

Chew, K. W. et al., "Development of Low Temperature Precursors to Barium Aluminosilicates," Presented at the Materials Research Society Fall 1992 Meeting, Boston, Mass. (Nov. 30, 1992); Poster No. R3.15.

Spindler, R. et al., "Investigations of a Siloxane–Based Polymer Electrolyte Employing $^{13}C$, $^{29}Si$, $^7Li$, and $^{23}Na$ Solid-State NMR Spectroscopy," J. Am. Chem. Soc. 110:3036–3043, 1988.

Albinsson, I. et al., "Ionic conductivity in poly(ethylene oxide) modified poly(dimethylsiloxane) complexed with lithium salts," Polymer 32:2712–2715, 1991.

Mei, H. L. et al., "Ionic Conductive Polymers Based on (Abstract continued on next page.)

Crosslinked Elastic Siloxane-Ethylene Oxide Copolymers," *Mol. Cryst. Liq. Cryst.* 160:321–330, 1988.

Popall, M. et al., "Inorganic-Organic Copolymers as Solid State Li+ Electrolytes," *Electrochemica Acta* 37(9):1593–1597, 1992.

Ganapathiappan, S. et al., "Synthesis, Characterization, and Electrical Response of Phosphazene Polyelectrolytes," *J. Am. Chem. Soc.* 111:4091–4095, 1989.

Arnanda, P. et al., "Poly(ethylene oxide)-Silicate Intercalation Materials," *Chem. Mater.* 4:1395–1403, 1991.

Zhou, G. et al., "Cation transport polymer electrolytes. Siloxane comb polymers with pendant oligo-oxyethylene chains and sulphonate groups," *Poly. Commun.* 30:52–55, 1989.

Primary Examiner—James J. Seidleck
Assistant Examiner—Mary Critharis
Attorney, Agent, or Firm—Christensen, O'Connor, Johnson & Kindness

[57] ABSTRACT

Tetra(alkylene oxide)silicate polymers are obtained by reacting pentacoordinate and hexacoordinate silicon complexes with tetra(alkylene) glycol, generally in accordance with the following reaction, as represented by the hexacoordinate species:

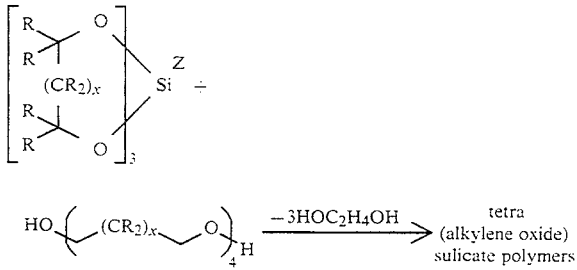

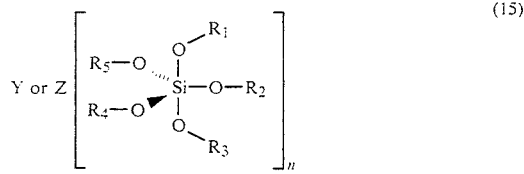

The resulting polymers are represented by the following general formula:

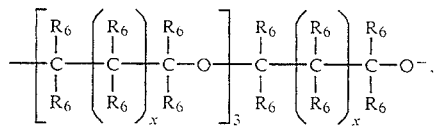

wherein $R_1$ through $R_5$ contain a carbon atom bonded directly to an oxygen atom of the above structure and are independently selected from the group consisting of

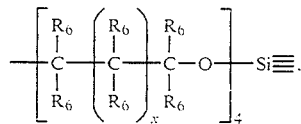

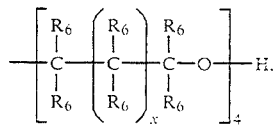

$$\left[\begin{array}{c} R_6 \\ | \\ -C- \\ | \\ R_6 \end{array} \left(\begin{array}{c} R_6 \\ | \\ C \\ | \\ R_6 \end{array}\right)_x \begin{array}{c} R_6 \\ | \\ C-O \\ | \\ R_6 \end{array} \begin{array}{c} R_6 \\ | \\ C \\ | \\ R_6 \end{array} \left(\begin{array}{c} R_6 \\ | \\ C \\ | \\ R_6 \end{array}\right)_x \begin{array}{c} R_6 \\ | \\ C-O^- \\ | \\ R_6 \end{array}\right]_3$$

can be taken together to be —$CH_2CH_2$—, with the proviso that at least three or $R_1$ through $R_5$ must be,

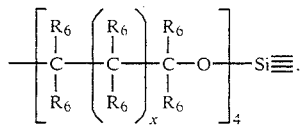

x is 0 or 1, each $R_6$ is independently selected from H, OH, $C_{1-6}$alkyl, O—$C_{1-6}$alkyl, $C_{2-6}$alkene, $C_{6-12}$aryl, $C_{1-6}$hydroxyalkyl, $C_{1-6}$thioalkyl, $C_{2-12}$alkoxyalkyl, $C_{3-20}$heteroaromatic, and combinations thereof, wherein each R group may also contain non-carbon elements such as Si, Sn, Ge, P, and the like; Y is monovalent Z is multivalent cationic, preferably dicationic and n is from 2 to 10,000. Methods for producing such polymers starting with silica or silicon-containing complexes are disclosed.

16 Claims, No Drawings

ION CONDUCTING POLYMERS

This application is a continuation application based on prior copending application Ser. No. 08/027,120, filed on Mar. 4, 1993, now abandoned which is a continuation-in-part of U.S. application Ser. No. 07/792,214, filed Nov. 12, 1991, now U.S. Pat. No. 5,216,155, which is a continuation-in-part of U.S. application Ser. No. 07/509,022, filed Apr. 13, 1990, now U.S. Pat. No. 5,099,052.

FIELD OF THE INVENTION

The present invention relates to ion conducting polymers formed from complexes containing at least one silicon atom, and to the preparation of such polymers from penta- and hexa-coordinate silicon complexes or from silica (in various chemical and mineral forms).

BACKGROUND OF THE INVENTION

Silicon-based chemicals are used in a wide variety of applications, such as in biocides, stain- and dirt-resistant polymers for carpets, advanced ceramics for aerospace applications and electronic components. The market for silica and other silicon-containing materials amounts to several billion dollars per year. One important aspect of this market, not immediately evident even to a first-hand observer, is the fact that all silicon-based materials beyond sand are produced by high temperature metallurgical processing technologies that: (1) add considerable cost to the typical product; (2) limit the scope of applications, and (3) offer limited opportunity for growth because of the maturity of the process.

Silicon products may be derived from the carbothermal reduction of silica to silicon metal:

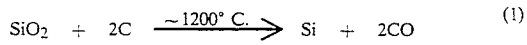  (1)

The resulting metallurgical grade silicon (90–98% purity) must then undergo further processing to make other products. For example, to make many of the industrially useful (high purity) forms of silica (e.g., fumed or electronics grade silica), it is necessary to first react the Si metal produced in reaction (1) with $Cl_2$ or HCl to make $SiCl_4$ which can then be burned (e.g., reaction 4):

$$Si + 2Cl_2 \rightarrow SiCl_4 \quad (2)$$

$$Si + HCl \rightarrow HSiCl_3 + SiCl_4 \quad (3)$$

$$SiCl_4 + H_2O + O_2 \rightarrow SiO_2 + HCl + HClO_x \quad (4)$$

Carbothermal reduction requires high heat and specialized equipment. The result is an energy and equipment intensive process. Reaction of silicon with chlorine or HCl also requires specialized, expensive equipment to deal with toxic and corrosive materials. Despite these considerable drawbacks, because the basic technology was developed late in the last century and early in this century, all of the processing problems have been worked out. This, coupled with economies of scale, makes this approach to the production of fumed and electronics grade silica commercially successful.

The production of silicon-based chemicals follows somewhat similar chemistry. Most silicone polymers derive from the "Direct Process":

  (5)

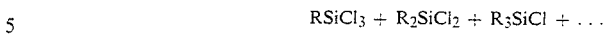

This simple reaction only works well when RCl is MeCl or PhCl. When it is MeCl, the major product is $Me_2SiCl_2$, which is hydrolyzed and polymerized to give polydimethylsiloxane, the basic silicone polymer:

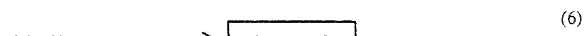  (6)

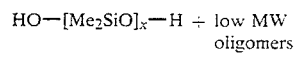

wherein n is 3–5 and x<100

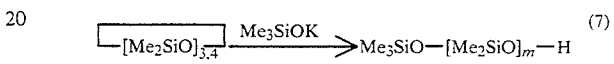  (7)

The above reactions, when coupled with standard organic chemistry reactions, and some special derivatives and processing procedures, provide the basis for the major portion of the silicone and silicon chemicals industry. It is surprising that there are few, if any, alternate methods for producing silicon-based polymers. If there were, and these new methods provided commercially competitive materials even a fraction as successful as the silicone polymers, the rewards would be exceptional. Preferably, these new methods should also involve an inexpensive and readily available starting material. In view of this, silica is an attractive starting material for producing silicon-containing species, such as those described above.

Silica, $SiO_2$, is the most common material found in nature. As sand, it is a basic ingredient in building materials, the manufacture of low-tech glass products and ceramics. In purer forms, it is used as an abrasive (e.g., toothpaste) and as a drying and texturizing agent in food and food-related products. It is also used in the manufacture of electronic materials and optical products.

Silica is also a feedstock material used for the manufacture of silicon-based chemicals. Synthetic routes stemming from the use of silica gel offer the important attribute of being very inexpensive (research grade silica sells for ~$15/kg or less). Additionally, silica gel is very easy to handle due to its relative non-reactivity. Industrial fused silica sells for less than $1/kg, and can be used here.

On the other hand, because of its low reactivity, there are few simple, low-temperature methods of chemically modifying silica. One such method is dissolution in base to give sodium silicate:

$$NaOH + SiO_2 \rightarrow Na_4SiO_4 \quad (8)$$

Unfortunately, this reaction has limited application for the formation of useful feedstock chemicals. The recent work of Kenny and Goodwin [Inorganic and Organometallic Polymers, N. Zeldin et al., *ACS Symposium Series* 360, 238 (1987)] on silicic acid esterification provides one successful transformation:

$$Na_4SiO_4 + HCl \rightarrow NaCl + \text{"}Si(OH)_4\text{"} \quad (9)$$

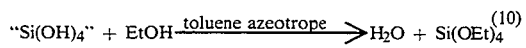

Si(OEt)$_4$, currently produced by reaction of EtOH with SiCl$_4$, reaction (11), is used commercially to form fumed and electronics grade silica.

It is also used to form optical glasses and boules for spinning fiber optics.

It has been reported that soluble complexes of silicon can be prepared from silica gel and catechol in water. These reports teach that the reactions of silica with 1,2 aromatic diols lead to the formation of hexacoordinate, monomeric silicon complexes:

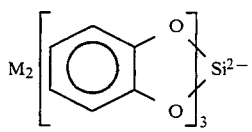

where M = Na, K, etc.

This approach was modified and refined by Corriu and co-workers by using basic methanol solutions under anhydrous conditions. A. Boudin, et. al., *Angew. Chem. Int. Ed. Engl,* 25(5):474–475 (1986). These stable salts could then be alkylated by strong nucleophiles, such as Grignard reagents, to form three (and frequently four) new silicon-carbon bonds:

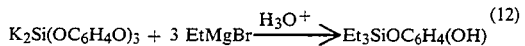

The problem with this approach is that the catechol complex, tris(1,2-dihydroxobenzoato) siliconate, is relatively expensive and can only be modified under forcing conditions using expensive reagents such as LiAlH$_4$, RMgBr, or RLi and the products are limited to tri- or tetrasubstituted silicon. Consequently, its large scale utility is limited. Furthermore, ready formation of mono- and dialkyl derivatives was not possible.

The inventions described in prior related U.S. Pat. Nos. 5,099,052 and 5,216,155 resulted from an exploration into methods of making more reactive complexes of silica using aliphatic 1,2- or 1,3-diols, such as ethylene glycol, instead of catechol. Thus, one aspect of the present invention, described in greater detail hereinbelow, involves the conversion of these novel silicon complexes, formed by a reaction between silica and 1,2- or 1,3-aliphatic diols, into commercially useful polymeric materials. These complexes have been determined to contain one or more anionic pentacoordinate silicon atoms when a monovalent counterion is involved and to contain an anionic hexacoordinate silicon atom when divalent or higher valency counterions are involved.

Other pentacoordinate and hexacoordinate silicon species have also been reported. For example, U.S. Pat. No. 3,455,980 discloses pentacoordinate silicon complexes of vicinal aliphatic diols, including ethylene glycol, formed from a compound of the formula (R'O)$_4$Si in the presence of excess aliphatic diol and an amine. U.S. Pat. Nos. 4,632,967, 4,577,003, and 4,447,628 are also directed to penta-coordinate silicates, all of which have structures that are different from those of the present invention. Other publications related to the field include "Pentacoordinate Silicon Derivatives. IV.1 Alkyl-ammonium Siliconate Salts Derived from Aliphatic 1,2-Diols" [C. L. Frye, *J. Am. Chem. Soc.* 92(5):1204–1210 (1970)]; "Cyclic Pentaoxy Siliconates," R. R. Holmes et al., *Phosphorus, Sulfur and Silicon and the Related Elements* 42:1–13 (1989); "Reaction of Grignard Reagents With Dianionic Hexacoordinated Silicon Complexes: Organosilicon Compounds from Silica Gel," A. Boudin, et. al., *Angew. Chem. Int. Ed. Engl,* 25(5):474–475 (1986); "Reaction of Catechol with Colloidal Silica and Silicic Acid in Aqueous Ammonia," D. W. Barnum, *Inorganic Chemistry* 11(6):1424–1429 (1972); and "Pentacoordinate Silicon Compounds. V.1a Novel Silatrane Chemistry," C. L. Frye, et al., *J. Am. Chem. Soc.* 93(25):6805–6811 (1971).

In spite of previous work involving functionalization of silica and other work involving preparation of pentacoordinate and hexacoordinate silicon complexes, there has remained a need for new and improved ways of producing useful silicon compounds. As reported in prior related U.S. Pat. Nos. 5,099,052 and 5,216,155, silica can be made to react with aliphatic diols in the presence of a base and with removal of water during the reaction, to produce pentacoordinate or hexacoordinate silicon complexes, as shown in the following scheme:

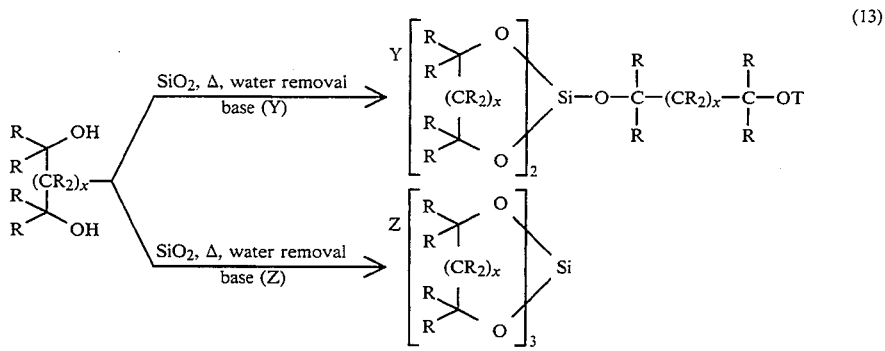

wherein x is 0 or 1, each R and R$_2$ is independently selected from H, OH, C$_{1-6}$alkyl, O—C$_{1-6}$alkyl, C$_{2-6}$alkene, C$_{6-12}$aryl, C$_{1-6}$hydroxyalkyl, C$_{1-6}$thioalkyl, C$_{2-12}$alkoxyalkyl, C$_{3-20}$heteroaromatic, and combinations thereof, wherein the R groups may also contain other, non-carbon elements such as Si, Sn, Ge, P, and the like; T is H or

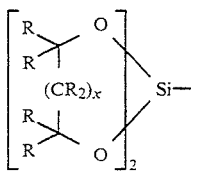

Y is monovalent cationic, and Z is multivalent cationic, preferably dicationic. The product of the above reaction is a monomeric (T=H) or dimeric (T=other than H) silicon complex.

The present invention provides for the conversion of penta- and hexacoordinate silicon complexes, such as those described above, into ion conducting silicon polymers.

SUMMARY OF THE INVENTION

An object of the present invention is to enable preparation of useful silicon-containing polymers using silica or silicon-containing complexes as starting materials.

It is another object of the present invention to obtain silicon-containing compounds that are further reacted to produce ion conducting silicon polymers.

It is yet another object of the present invention to provide a method for making ion conducting silicon polymers starting with silica or silicon-containing complexes, using simple and inexpensive reactions.

The above and other objects of the present invention, as will hereinafter become more readily apparent, have been achieved by the discovery that ion conducting tetra(alkylene oxide)silicate polymers can be obtained by reacting pentacoordinate and hexacoordinate silicon complexes with tetra(alkylene) glycol, generally in accordance with the following reaction, as represented by the hexacoordinate species:

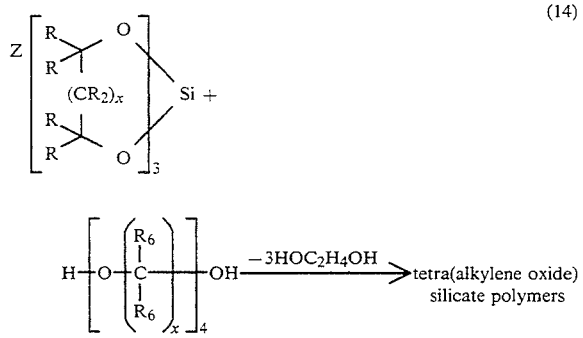

(14)

where x is 1, 2 or 3, and $R_6$ and Z are as defined below.

Preferred polymers of the invention may be represented by the following general formula:

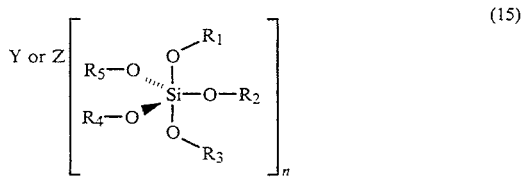

(15)

wherein $R_1$ through $R_5$ contain a carbon atom bonded directly to an oxygen atom of the above structure and are independently selected from the group consisting of

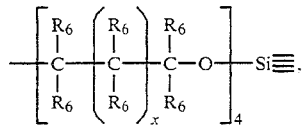

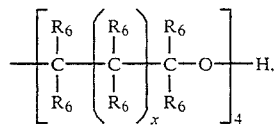

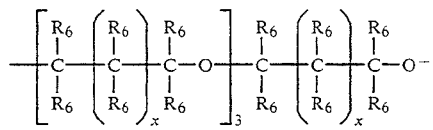

can be taken together to be —$CH_2CH_2$—, with the proviso that at least three of $R_1$ through $R_5$ must be,

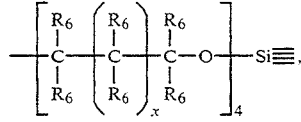

x is 0 or 1, each $R_6$ is independently selected from H, OH, $C_{1-6}$alkyl, O—$C_{1-6}$alkyl, $C_{2-6}$alkene, $C_{6-12}$aryl, $C_{1-6}$hydroxyalkyl, $C_{1-6}$thioalkyl, $C_{2-12}$alkoxyalkyl, $C_{3-20}$heteroaromatic, and combinations thereof, wherein each R group may also contain other, non-carbon elements such as Si, Sn, Ge, P, and the like; Y is monovalent cationic, Z is multivalent cationic, preferably dicationic and n is from 2 to 10,000.

In a presently particularly preferred embodiment, polymers of the invention are formed from the reaction of pentacoordinate and hexacoordinate silicon complexes of the structures set forth above, wherein x is 0 and R is H, with tetraethylene glycol to form tetra(ethylene oxide)silicate polymers.

The polymers of the invention have been found to form clear, viscous to plastic polymeric materials having ion conducting properties, and have an anion in and as part of the backbone structure of the polymer. The polymers are useful as ion conducting polymers, photochromic polymers when cations permit charge transfer, ceramic and glass precursors, offer non-linear optical properties when the cation permits charge transfer, electrochromic materials when the cation can be reduced or oxidized, ion conducting membranes and the like.

DETAILED DESCRIPTION OF THE INVENTION

The present invention is based on a discovery that ion conducting polymers can be formed directly from silica or from silicon intermediate complexes, such as those disclosed in prior related U.S. Pat. Nos. 5,099,052 and 5,216,155.

Silicon Intermediate Complexes

The following scheme depicts an exemplary reaction starting with silica to form an intermediate complex of the present invention in the presence of the monovalent cation K+:

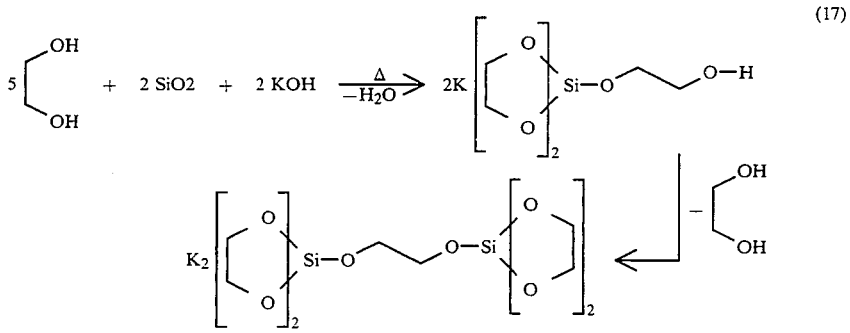

The following scheme depicts an exemplary reaction starting with silica to form a complex of the present invention in the presence of the divalent cation Ba++:

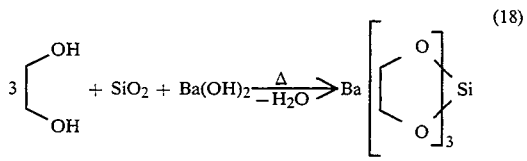

The starting materials, an aliphatic glycol, silica, and a base, may be obtained from commercial sources, such as the Sigma Chemical Company and the Aldrich Chemical Company, or may be synthesized using available starting materials and known reactions.

Generally speaking, a molar excess of an aliphatic diol is added to silica and a base, a suitable solvent is added, and the mixture is allowed to react with water being removed continuously. It is possible to run the reaction in excess reactant as solvent. The molar ratio of diol:silica:base is typically 3–5:1–3:1–3.

The base used in the reaction may be an alkali metal hydroxide or oxide, such as lithium hydroxide, sodium hydroxide, potassium hydroxide, or cesium hydroxide, an alkaline earth metal hydroxide or oxide, such as barium hydroxide, magnesium hydroxide, calcium hydroxide, barium oxide, magnesium oxide, calcium oxide, and the like. Surprisingly, when the counterion is monocationic, a mixture of monomeric and dimeric pentacoordinate silicon species is produced, whereas when the counterion is dicationic (e.g., $Mg^{2+}$, $Ca^{2+}$, $Ba^{2+}$, $Sr^{2+}$, $Ni^{2+}$, or $Co^{2+}$), a monomeric hexacoordinate species is produced. Tricationic or higher valent cationic species may also produce hexacoordinate species. The base will generally provide the cation, Y or Z, in the final product.

As far as the inventors are aware, there are no specific requirements to be imposed on the cation, and a chemist will readily be able to select any of a variety of cations that will work for purposes of the present invention. However, many transition metal cations will be reduced if conditions are not suitable and care in choice of reaction conditions should be exercised with this in mind. It is preferred that the cation be derived from an alkali metal or alkaline earth metal, but it may also be derived from other chemical species.

An example of another chemical species that may serve as a cation in the silicon complexes is a quaternary salt. Suitable quaternary salts have the general structure:

$$R'_4 EX$$

wherein E is N, P, or Sb; each R' is independently $C_{1-4}$alkyl, and X is an anion such as hydroxide or some species that generates OH' on reaction with water. Exemplary divalent cations are: $Mg^{2+}$, $Ca^{2+}$, $Ba^{2+}$, $Sr^{2+}$, $Ni^{2+}$, and $Co^{2+}$. The diol that is employed may be any one having the formula:

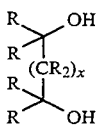

wherein x is 0 or 1, and each R is independently selected from H, OH, $C_{1-6}$alkyl, $C_{1-6}$alkoxy, $C_{2-6}$alkene, $C_{6-12}$aryl, $C_{l6}$hydroxyalkyl, $C_{1-6}$thioalkyl, $C_{2-12}$alkoxyalkyl, $C_{3-20}$heteroaromatic, and combinations thereof, wherein R may have one or more (preferably 1-3) non-carbon elements, such as Si, Sn, Ge, and P.

The alkyl moieties may be straight chain, branched, and/or cyclic. Exemplary nonlimiting alkyl moieties are: methyl, ethyl, propyl, i-propyl, cyclopentyl, 2-methylbutyl, and the like.

The alkene moieties may be straight chain, branched and/or cyclic. Nonlimiting examples are the mono, di, and polyunsaturated analogs (where possible) of the above-listed alkyl groups having greater than two carbon atoms.

The aryl groups are generally aromatic hydrocarbon moieties that have 6 to 12 carbon atoms. The aryl groups may be attached directly to the diol or be attached by way of an intervening alkyl moiety. Nonlimiting examples of the aryl group are: benzyl, phenyl, and the like.

The hydroxyalkyl groups may be any straight chain, branched, and/or cyclic $C_{1-6}$alkyl group substituted with one or more (preferably 1-3) hydroxyl groups. Nonlimiting examples are 1-hydroxyethyl, 2-hydroxyethyl, 1-hydroxypropyl, and the like.

The thioalkyl groups may be any straight chain, branched, and/or cyclic $C_{1-6}$alkyl attached to the diol by way of a sulfur atom. Nonlimiting examples are any of the alkyl moieties described above attached by a sulfur atom to the diol.

The alkoxyalkyl groups may be any ether moiety containing 2 to 12 carbon atoms. Nonlimiting examples are methoxymethyl, ethoxymethyl, methoxyethyl, and the like.

The heteroaromatic groups may be any $C_{3-20}$ group (preferably $C_{3-8}$) containing one or more (preferably 1 or 2) heteroatoms (preferably O, N, and/or S). Nonlimiting examples are groups derived from pyridine, thiophene, pyrazine, triazine, etc.

Preferably, the diol is unsubstituted or is independently substituted by 1-3 nonhydrogen substituents. Also, the preferred substituents are $C_{1-6}$alkyl or $C_{2-6}$alkenyl. Further, the substituents are preferably located on different carbon atoms of the complex.

Some combinations of substituents will not be desirable due to incompatibility, steric crowding, and/or instability under reaction conditions. One of ordinary skill will be able to determine these combinations based on standard synthetic considerations and/or routine experimentation.

Optically active diols are also contemplated; these diols may be resolved before use in the reaction, or may be used as a mixture of racemates. Similarly, the final products formed by using a diol with an optically active carbon atom may be resolved during purification or may be used as a mixture of stereoisomers.

Vicinal diols are preferred as the diols herein. However, under some circumstances, the hydroxyl groups may have a 1,3 orientation on the diol, depending upon the flexibility of the diol ligand, etc.

Any grade or form of silica may be employed in the reactions. A preferred silica is 10-800 mesh with minimal organic impurities. However, even beach sand can be used.

The basic reaction starting with silica that is described above may be conducted in a variety of solvents. Preferred solvents are higher boiling alcohols such as ethylene glycol, 2-aminoethanol, amyl alcohol, 2-ethoxyethanol, and the like. However, other solvents are also possible, such as DMSO, sulfolane, N-methyl pyrrolidone.

The reaction will generally be conducted at from ambient temperature to higher temperatures. Conveniently, the reaction may be conducted at the boiling point of the solvent that is employed. For most purposes, the upper limit of the temperature range will be approximately 200° C. Preferably, the temperature range will be from about 30°-170° C. Most desirably, the temperature will range from about 80° C. to 150° C.

In order to obtain the pentacoordinate and hexacoordinate complexes described in related U.S. Pat. Nos. 5,099,052 and 5,216,155, it is important that substantially all water that is formed during the reaction be removed as it is formed. It has been found that if the water is not removed, the products described herein are not obtained, as shown by Example 9, below. Conveniently, the water may be removed by azeotropic distillation; the precise temperature at which water can be azeotropically removed will depend upon the solvents which are used and other conditions, as will be readily understood by a synthetic chemist. The water may also be removed by known water-scavenging species or by any standard membrane transport protocol.

The reaction will typically be carried out for a time period of from a few minutes (e.g., twenty minutes) up to 2-4 days, as necessary.

The final product will often separate out of the reaction mixture as a precipitate on cooling; however, it may also remain dissolved in the reaction mixture and may be precipitated by addition of a nonsolvent such as acetonitrile. Alternatively, the product may be reacted directly to form the polymers of the invention, as hereinafter further described, without precipitation, isolation or purification. The product may be isolated and purified by any of a variety of standard methodologies. For example, the product may be taken up in a solvent, filtered, concentrated, and then crystallized. The crystallized product may then be recrystallized from a suitable solvent system. In some situations, it may be necessary to carry out column chromatography or another purification procedure to aid in the purification of the desired product. In a preferred embodiment, ethylene glycol is reacted with silica in the presence of an alkali metal hydroxide or oxide to produce a dimeric pentacoordinate or monomeric hexacoordinate silicon complex, as depicted below:

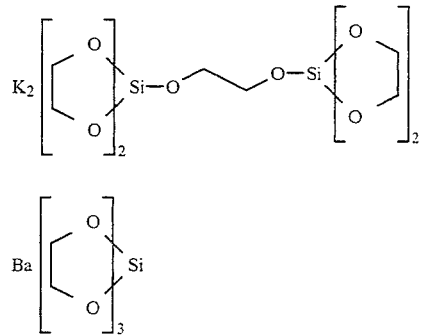

Other preferred reactants, etc., are summarized in the following Table:

| Diol | Base | Solvent | Reaction Temp (°C.) | Product |
|---|---|---|---|---|
| 1,2-ethanediol | MOH<br>M = Li, Na, K, Cs | $HOCH_2CH_2OH$ | 100-200 | $K_2Si_2(OCH_2CH_2O)_5$ |
| 1,2-ethanediol | $M(OH)_2$<br>M = Mg, Ca, Sr, Ba | $HOCH_2CH_2OH$ | 100-200 | $MSi(OCH_2CH_2O)_3$ |
| 1,2-ethanediol | $Ca(OH)_2$ | $H_2NCH_2CH_2OH$ | 100-200 | $CaSi(OCH_2CH_2O)_3$ |
| 1,2-ethanediol | $Ca(OH)_2$ | $HSCH_2CH_2OH$ | 100-200 | $CaSi(OCH_2CH_2O)_3$ |
| 1,2-ethanediol | $Ca(OH)_2$ | $EtOCH_2CH_2OH$ | 100-200 | $CaSi(OCH_2CH_2O)_3$ |
| 1,2-ethanediol | $Ca(OH)_2$ | $H(OCH_2CH_2)_2OH$ | 100-200 | $CaSi(OCH_2CH_2O)_3$ |
| 1,2-ethanediol | $Ca(OH)_2$ | $HN(CH_2CH_2OH)_2$ | 100-200 | $CaSi(OCH_2CH_2O)_3$ |
| 1,2-ethanediol | $Ca(OH)_2$ | $O(CH_2CH_2OH)_2$ | 100-200 | $CaSi(OCH_2CH_2O)_3$ |
| Pinacol | MOH<br>M = Li, Na, K, Cs | $HOCH_2CH_2OH$ | 100-200 | $M_2Si_2(OCMe_2CMe_2O)_5$ |
| Glycerol | MOH<br>M = Li, Na, K, Cs | $HOCH_2CH_2OH$ | 100-200 | $M_2Si_2(OCH_2CH(CH_2OH)O)_5$ + polymer |
| 1,2-propanediol | MOH<br>M = Li, Na, K, Cs | $HOCH_2CH_2OH$ | 100-200 | $M_2Si_2(OCH_2CH(CH_3)O)_5$ |
| 1,3-propanediol | MOH<br>M = Li, Na, K, Cs | $HOCH_2CH_2OH$ | 100-200 | $M_2Si_2(OCH_2CH_2CH_2O)_5$ |

| Diol | Base | Solvent | Reaction Temp (°C.) | Product |
|---|---|---|---|---|
| 1-amino-2,3-propanediol | MOH<br>M = Li, Na, K, Cs | HOCH$_2$CH$_2$OH | 100-200 | M$_2$Si$_2$(OCH$_2$CH(CH$_2$NH$_2$)O)$_5$ |
| cyclohexane (Cyc) 1,2-diol | Ca(OH)$_2$ | HOCH$_2$CH$_2$OH | 100-200 | CaSi[1,2-(O)$_2$Cyc]$_3$ |
| 1,2-diphenylethane 1,2-diol (dip) | Ca(OH)$_2$ | HOCH$_2$CH$_2$OH | 100-200 | CaSi[1,2-(O)$_2$Cyc]$_3$ |

Additional details on the basic reaction parameters as applied to specific reactants are provided in the Examples section hereinbelow.

Polymer Formation

As set forth above, the ion conducting tetra(alkylene oxide)silicate polymers of the invention are obtained by reacting pentacoordinate and hexacoordinate silicon complexes with tetra(alkylene) glycol, generally in accordance with the following reaction, as represented by the hexacoordinate species:

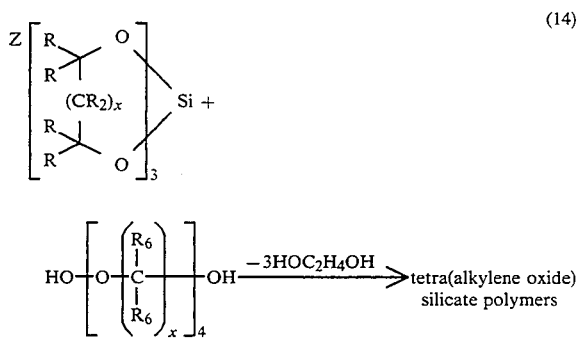

Alternatively, the tetra (alkylene oxide) silicate polymers may be obtained in a "one pot" reaction directly from silica, as is described in more detail below.

The lability of the coordinated ethanediolate ligand affords access to new materials through facile ligand exchange with higher chain 1,2-, 1,3-, 1,4- and higher diol chains, [1,3,4]. While both 1,2- and 1,3-diols either chelate Si to form monomers and dimers, the introduction of longer chains favors bridging coordination and promotes polymerization.

Preferred polymers of the invention may be represented by the following general formula:

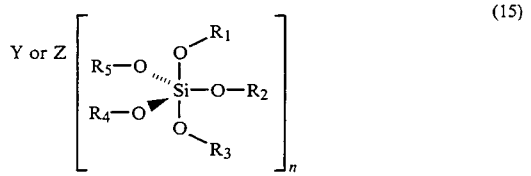

wherein R$_1$ through R$_5$ contain a carbon atom bonded directly to an oxygen atom of the above structure and are independently selected from the group consisting of

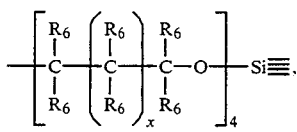

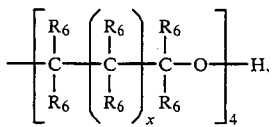

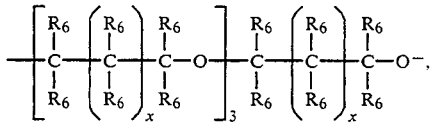

—CH$_2$OH and —CH$_2$O—, or R$_3$ and R$_4$ can be taken together to be —CH$_2$CH$_2$—, with the proviso that at least three of R$_1$ through R$_5$ must be,

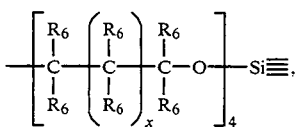

x is 0 or 1, each R$_6$ is independently selected from H, OH, C$_{1-6}$alkyl, O—C$_{1-6}$alkyl, C$_{2-6}$alkene, C$_{6-12}$aryl, C$_{1-6}$hydroxyalkyl, C$_{1-6}$thioalkyl, C$_{2-12}$alkoxyalkyl, C$_{3-20}$heteroaromatic, and combinations thereof, wherein each R group may also contain other, non-carbon elements such as Si, Sn, Ge, P, and the like; Y is monovalent cationic, Z is multivalent cationic, preferably dicationic and n is from 2 to 10,000.

In a presently particularly preferred embodiment, polymers of the invention are formed from the reaction of pentacoordinate and hexacoordinate silicon complexes of the structures set forth above, wherein x is 0 and R$_6$ is H, with tetraethylene glycol to form tetra(ethylene oxide)silicate polymers of the formulas:

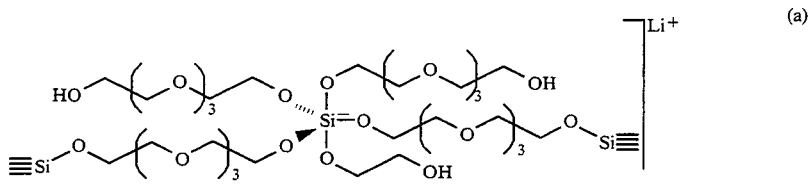

(a)

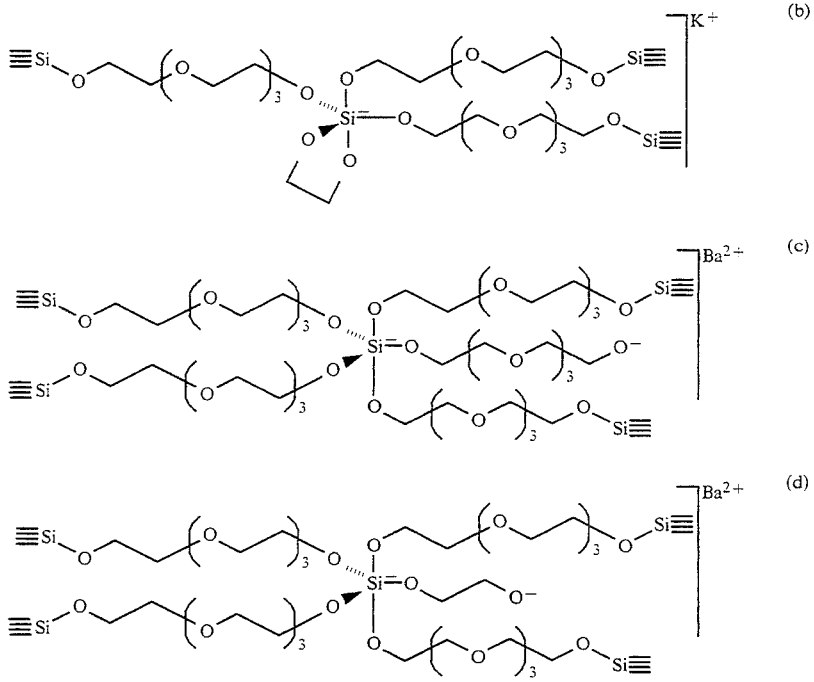

The purely ionic character of the alkali metal complexes, demonstrated by single crystal X-ray diffraction, and both solution and solid state 29Si NMR, indicated that polymers prepared from ethylene oxide-bridged silicate oligomers would be ion conducting with the anionic silicon counterions embedded in the backbone and serving as crosslinking centers.

The polymeric compounds are prepared from the corresponding intermediate ethane(diolato)silicate salts, such as those described above, by heating a mixture of the ethane(diolato)silicate with polyalkylene oxide under a nitrogen atmosphere until the precursor completely dissolves. The mixture is then subject to vacuum distillation at elevated temperatures for a sufficient period of time to complete distillation of exchanged alkylene diol ligands. The mixture may be further heated to remove unreacted polyalkylene oxide. Cooling of the mixture then produces the clear, viscous liquid polymer. Further treatment by vacuum distillation may be employed, if desired, to produce plastic, rubbery or hard solids. Further, the viscous liquid polymers may be cured to hard, translucent films, such as by heating in a tube furnace at elevated temperatures for extended periods.

The polymers in accordance with the invention have a polyalkylene oxide-pentacoordinate silicate backbone that remains amorphous at low temperatures, and are thermally stable from −70° C. to 200° C. The precise nature of the polymers is dependent on the extent of vacuum distillation, and range from compounds containing mixtures of monodentate and bidentate ligands to fully cross-linked materials.

The invention now being generally described, the same will be better understood by reference to certain specific examples which are included herein for illustrative purposes only, and are not intended to be limiting of the present invention.

EXAMPLES

A. General

1. Procedures. All operations were carried out with the careful exclusion of extraneous moisture. Air-sensitive materials were manipulated using standard Schlenk and glovebox techniques. $^1$H, $^{13}$C and $^{29}$Si spectra NMR spectra were taken in $CD_3OD$ and referenced to TMS. All chemicals were purchased from standard vendors and used as received, except the diols, which were distilled under nitrogen before use.

2. Equipment. Infrared spectra were recorded on an Mattson Galaxy spectro-photometer. Nuclear magnetic resonance data were collected on a Varian 300 MHz spectrometer. Elemental analyses were performed by Galbraith Laboratories in Knoxville, Tenn.

B. Materials

1. Preparation of $K_2Si_2(OCH_2CH_2O)_5$. 13.8 grams of 400 mesh silica gel (0.23 mol) and 14.8 grams (0.26 mol) of potassium hydroxide (85%) were weighed into a 500 mL round bottom flask. 125 mL of freshly distilled (from $Mg/MgI_2$) EtOH and 250 mL of distilled ethylene glycol were added to the flask and the mixture was heated to boiling. The ethanol fraction was distilled off to remove (by azeotrope) any water formed during the reaction. The mixture was then heated further until the solution appeared homogeneous. Partial dissolution of the silica occurred during this period. Distillation was continued to remove the major fraction of the excess ethylene glycol and water formed during reaction. During distillation, most of the silica dissolved. Upon cooling, the remaining colorless liquid turned to a sticky white solid mass. This mass was taken up in 350 mL of freshly distilled methanol and filtered through a Celite-covered frit. The flitrate was concentrated in vacuo to ~20 mL after which portions of dry acetonitrile were added slowly to precipitate out a fine white powder. The precipitate was then collected on a glass frit and washed with 3 × 200 mL of acetonitrile. Recrystallization from methanol and acetonitrile/ether resulted in a pure white powder which was vacuum-dried at 130° C. This resulted in 90 g (0.21 mol) of product or 90% yield. NMR: $^1$H, 3.4 ppm (under solvent peak); $^{13}$C, 61.1, 64.3 ppm; $^{29}$Si, −103.0 ppm. Elemental analysis, calc. (found) %C, 27.53 (27.63); %H, 4.98 (4.64); %Si, 13.60 (12.92); %K 17.84 (17.99); %O by difference, 37.01 (36.81).

2. Production of Functionalized Silicon-Containing Species. When $K_2Si_2(OCH_2CH_2O)_5$ is added slowly to neat acetic anhyride and heated, initially, KOAc can be filtered off after the reaction is cooled. Acetyl chloride can also be used. Removal of excess anhydride and 1,2-ethanediacetate under vacuum leads to a white solid which can be characterized as $Si(O_2CCH_3)_4$. Treatment of $K_2Si_2(OCH_2CH_2O)_5$ with two equivalents of HCl, followed by filtration of the KCl leads to the isolation of a neutral tetracoordinate, polymeric silicon compound with the empirical formula $Si(OCH_2CH_2O)_2$, which is in equilibrium with the excess ethylene glycol formed during neutralization to form ring opened diols, e.g., $Si(OCH_2CH_2O)_2(OCH_2CH_2OH)_2$, that can be used in place of $Si(OEt)_4$ for sol-gel processing of silica containing glasses. At higher concentrations, the $Si(OCH_2CH_2O)_2(OCH_2CH_2OH)_2$ species are in equilibrium with oligomeric/polymeric forms whose rheology can be controlled by removal of excess ethylene glycol or solvent addition to form coatable or spinnable materials that can serve as precursors to silicon-containing ceramics. These neutral four coordinate silicon-containing species can be used as precursors to other silicon containing species using techniques common to the polysiloxane synthetic chemist.

3. Preparation of $Li_2Si_2(OCH_2CH_2O)_5$. A procedure similar to that used for the potassium derivative was employed using 5.00 g (0.083 mol) of silica and 1.98 g (0.083 mol) of LiOH. When the "polymeric" portion of the product, that portion which is not immediately soluble, was left stirring for 1–2 days in methanol, it dissolved quantitatively. The resulting methanol-soluble material was recrystallized from methanol and acetonitrile/ether and vacuum-dried at 130° C. This resulted in 26.2 g (71 mmol) of product or 85% yield. $^{13}$C, 61.2, 64.4 ppm; $^{29}$Si, −102.9 ppm.

4. Preparation of $Na_2Si_2(OCH_2CH_2O)_5$. Procedures identical to those described for the preparation of the potassium salt were used except 3.33 g (83 mmol) of NaOH were used. Again, stirring for 1–2 days in methanol resulted in complete dissolution. The methanol-soluble material could be recrystallized as above and dried in vacuum at 130° C. This resulted in 26 g (75 mmol) of product or 90% yield. NMR (CD$_3$OD): $^1$H, 3.36 ppm; $^{13}$C, 63.2 ppm; $^{29}$Si, −103.3 ppm.

5. Preparation of $CsSi(OCH_2CH_2O)_2(OCH_2CH_2OH)$. Procedures identical to those described for the preparation of the potassium salt were used except 8.74 g (83 mmol) of CsOH were used. The product in this instance was entirely soluble in ethanol. The product was precipitated out by addition of acetonitrile. Although almost all of the silica dissolved, the isolated yield (without drying) was only 53%. NMR (CD$_3$OD): $^1$H, 3.4 ppm (under solvent peak); $^{13}$C, 63.2 ppm; $^{29}$Si, −103.1 ppm. Elemental analysis, calc. (found) %C, 20.72 (21.06); %H, 3.63 (3.83); %Si, 8.58 (8.21); %Cs 39.38 (38.84); %O by difference, 27.32 (27.06). IR (nujol) u O—H=3300.

6. Exchange of Pinacol for Ethylene Glycol. 1.5 g (3.46 mmol) of $K_2Si_2(OCH_2CH_2O)_5$ were mixed with 80 mL of freshly distilled pinacol (added as a solvent). The reaction mixture was then heated under $N_2$. The mixture melted, the silicate dissolved and heating was continued until 65 mL of a mixture of ethylene glycol and pinacol were distilled off. On cooling, the remaining liquid became a white solid. Excess pinacol was washed away using 2×50 mL of acetonitrile. The remaining white material was then dissolved in methanol and recrystallized as above. The yield was essentially quantitative. The product is expected to be $K_2Si_2(OCMe_2CMe_2O)_5$. NMR (CD$_3$OD): $^1$H, 3.4 ppm (under solvent peak); $^{13}$C, 75.8, 26.5, 25.9 ppm; $^{29}$Si, −109 ppm.

7. Exchange of 1,3-Propanediol for Ethylene Glycol. 5.0 g (11.5 mol) of $K_2Si_2(OCH_2CH_2O)_5$ were mixed with 50 mL of freshly distilled 1,3-propanediol (added as a solvent). The reaction mixture was then heated under $N_2$. The silicate dissolved and heating was continued until a 35 mL mixture of ethylene glycol and propanediol was distilled off. The remaining solution was syringed into 50 mL of cold diethyl ether. The product collected as an oil at the bottom of the flask. The oil was cannulated into a 50 mL Schlenk flask and dried in vacuo to a clear glassy solid. This solid was dissolved in 15 mL of MeOH and syringed into 70 mL of acetonitrile to give a precipitate which was filtered off on a medium frit. NMR (CD$_3$OD): $^1$H 1.75 quintet, 1.74 quintet, 3.35 s, 3.66 triplet, 3.67 triplet, 5.13 s ppm; $^{13}$C, 60.0 and 36.3 ppm; $^{29}$Si, −107.2 ppm. The product can be partially polymeric.

8. Exchange of PEG$_4$ for Ethylene Glycol. 5.0 g (13.5 mmol) of $Li_2Si_2(OCH_2CH_2O)_5$ were mixed with 50 mL of ethylene glycol. The stirred solution was heated under $N_2$ until all of the lithium salt dissolved. 40 mL freshly distilled PEG$_4$ (tetraethylene glycol) were then added. The excess ethylene glycol was distilled off to give a clear yellow solution. 20 mL of PEG$_4$ were removed by distillation at reduced pressure to give a crude glassy polymeric product. The crude material was characterized by $^{13}$C NMR (CD$_3$OD): $^{13}$C, 73.6, 71.3, 64.3 and 62.1. The latter two peaks may indicate that some ethylene glycol remains. The structure may be polymeric.

9. Preparation of $BaSi(OCH_2CH_2O)_3$. 82.5 g of BaO and 30.03 g of $SiO_2$ were placed in a 1000 mL flask with 500 mL of ethylene glycol and stirred under $N_2$ for about 1 hour. The BaO and silica slowly dissolved upon continuous distillation under $N_2$. The contents of the flask turned slightly yellowish as the excess ethylene glycol was removed, taking along with it the three moles of water produced as a by-product. The solution also became increasingly viscous. After approximately 350 mL to 400 mL of ethylene glycol had been removed, crystalline material started to form. The contents of the flask were then left to cool overnight, resulting in the formation of a large solid mass. The product was broken up with a spatula and washed with 2×300 mL of acetonitrile, 2×300 mL of absolute ethanol, and finally with 300 mL of acetonitrile. The product was then vacuum dried at approximately 130° C. to obtain approximately 156 g of BaSi(OCH$_2$CH$_2$O)$_3$ as a white, fine flowing powder in a 90% yield by mass. The powder, a monomer, was soluble in methanol.

10. Preparation of CaSi(OCH$_2$CH$_2$O)$_3$. The procedure of Example 9 was repeated using 28.04 g of CaO, 30.04 g of SiO$_2$ and 500 mL of ethylene glycol as starting materials. Approximately 106 g CaSi(OCH$_2$CH$_2$O)$_3$ was obtained as a white, fine flowing powder in an 85% yield by mass. The powder, a monomer, was soluble in methanol.

11. Preparation of MgSi(OCH$_2$CH$_2$O)$_3$. The procedure of Example 9 is followed using MgO as a starting material to obtain MgSi(OCH$_2$CH$_2$O)$_3$ as a white, fine flowing powder in about a 30% yield by mass. The powder, a monomer, was soluble in methanol.

12. Preparation of NiSi(OCH$_2$CH$_2$O)$_3$. BaSi(OCH$_2$CH$_2$O)$_3$ prepared in accordance with Example 9 is dissolved in methanol and mixed with NiSO$_4$ in methanol. Insoluble BaSO$_4$ forms as a precipitate and is separated from the solution. NiSi(OCH$_2$CH$_2$O)$_3$ is recovered from the solution by removal of the solvent.

13. Preparation of CoSi(OCH$_2$CH$_2$O)$_3$. BaSi(OCH$_2$CH$_2$O)$_3$ prepared in accordance with Example 9 is dissolved in methanol and mixed with CoSO$_4$ in methanol. Insoluble BaSO$_4$ forms as a precipitate and is separated from the solution. CoSi(OCH$_2$CH$_2$O)$_3$ is recovered from the solution by removal of the solvent.

14. Preparation of M[Si(PEO$_4$)2.5]n. Lithium and potassium tetra(ethylene oxide)silicate polymers, {M[Si(PEO$_4$)$_{2.5}$]}n, were prepared in accordance with the following reaction (19), as described in detail below:

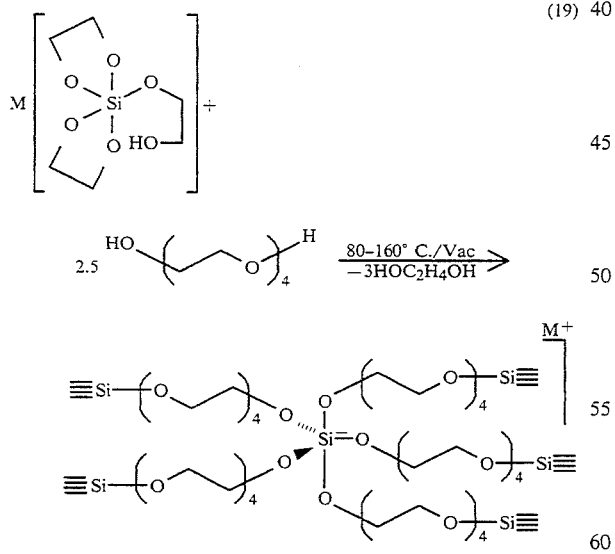

I (M = Li, IA; K, IB);
II (M = Ba);
III (M = Li); IV (M = K); V (M = Ba)

where M is Li or K. Syntheses were carried out under N$_2$ by standard schlenk line techniques in order to exclude atmospheric moisture. Lithium, potassium and barium tetra(ethylene oxide)silicate polymers (compounds III, IV and V) were prepared from the corresponding metal 1,2-ethanediolatosilicate salts I and II by the following procedure. A mixture of I or II (0.025 mol) and H$_2$PEO$_4$ (18 mL, 0.102 mol) was heated for 2 h at 120° C. under N$_2$ until the precursor completely dissolved. A vacuum distillation apparatus was attached and the solution was heated from 80°–120° C. over a three hour period under vacuum (0.03 mbar). The temperature was raised to 140° C. for 1 h to complete the distillation of exchanged ethanediol ligands. Further heating at 160° C. for 2.5 h removed any unreacted H$_2$PEO$_4$. Upon cooling, clear, golden brown, viscous polymer was obtained. Extended distillation at 180°–200° C. provided plastic, rubbery, or hard solids. Viscous liquid samples were cured to hard, translucent films 2 mm thick after heating in a tube furnace under static air at 196° C. for 2 h. The reaction of I (M=Li$^+$, IA; M=K$^+$, IB) or II with 3–4 equivalents of tetraethylene glycol (H$_2$PEO$_4$), as shown in Equation 19 for IA, quantitatively produced the clear, viscous product. These viscous to glassy materials are optically transparent. They offer room temperature ionic conductivities on the order of about 10$^5$ S cm$^{-1}$, good thermal stability and curing of solids at less than 200° C.

15. Preparation of Polymers Directly from SiO$_2$. Alternatively, the polymers III, IV, and V of Example 14 were prepared directly from SiO$_2$. In a typical experiment, LiOH, KOH or BaO (0.041 mol) was dissolved in excess 1,2-ethanediol at 110° C. and the H$_2$O by-product was distilled off To produce the Ba polymer, fused SiO$_2$ (0.041 mol) was added to the Ba$^{2+}$ solution and the temperature was raised to 200° C. and formed water removed by distillation to produce a clear, yellow solution. To this was added H$_2$PEO$_4$ (21.1 ml, 0.122 mol). The resulting solution was vacuum distilled as described in Example 14, to obtain barium tetra(ethylene oxide)silicate polymer. Equation 20 illustrates the net reaction with BaO:

$$BaO + SiO_2 + xsHOC_2H_4OH + \quad (20)$$

$$3H_2PEO_4 \xrightarrow[-xsHOC_2H_4OH]{80-160°C./Vac}$$

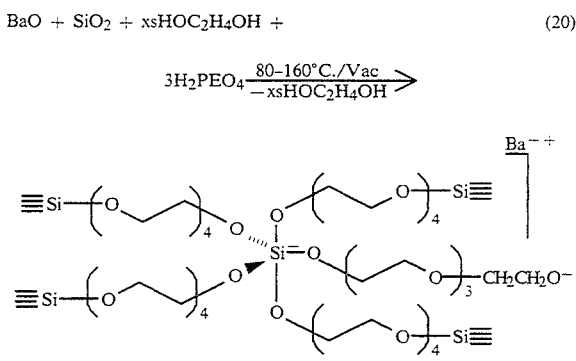

The above procedure was repeated substituting LiOH (0.041 mol) and KOH (0.041 mol) for the BaO, to obtain the corresponding lithium and potassium tetra(ethylene oxide)silicate polymers directly from SiO$_2$. The reaction does not proceed in the absence of 1,2-ethanediol, rather it requires the in situ formation of a 1,2-ethane(diolato)silicate intermediate, presumably similar to I or II, that undergoes ligand exchange with H$_2$PEO$_4$.

16. Characterization of M tetra(ethylene oxide)silicate polymers. The lithium, potassium and barium tetra(ethylene oxide)silicate polymers, III, IV, and V, were characterized by thermogravimetric analysis (TGA), differential scanning calorimet (DSC) and complex impedance measurements. TGA data were obtained using a TA Instruments 2950 Thermogravimetric Analyzer in the Hi Res mode. Ramp rates were 50° C./min to 1000° C. in $N_2$, using a Hi Res value of 4.0 and platinum pans. The balance gas was $N_2$ at a flow rate of 40 cc/min. The purge gas flow rate was 60 cc/min. Unless otherwise indicated, temperatures of thermal events are reposed at the maxima of 5%/ST plots. DSC data were obtained using a TA Instruments 2910 DSC with hermetically sealed aluminum pans. Samples were cooled to $-60°$ C., then heated to 600° C. at 10° C./min in $N_2$. The purge gas flow rate was 50 cc/min. Cyclic ns were also performed between $-70°$ C. and 50° C. Complex impedance measurements were made using a two probe technique at room temperature over the frequency range of 10 Hz to 100 kHz. The conductivity cell consisted of a cuvette which had Pt electrodes attached to opposite sides which were separated by a Teflon spacer. The polymer was poured into the cuvette and immediately covered. The sample was sufficiently fluid that no solvent was added. Direct current values were extrapolated from the data. Table 1 summarizes the properties derived from these experiments.

TABLE 1

| M | Compd. | $T_{dec}$, °C. | Ceramic Yield | $T_g$, °C. | R, kW | $k, 10^{-6} S\ cm^{-1}$ |
|---|---|---|---|---|---|---|
| Li+ | III | 175–350 | 7.88 | −25 | 133 | 3.3 |
| K+ | IV | 200–350 | 14.7 | −26 | 9.6 | 46 |
| $Ba^{2+}$ | V | 175–320 | 23.7 | −27 | 12.3 | 36 |

In liquid samples, the moderate viscosity and the TGA data indicate that the $PEO_4$ ligands are not all bidentate, and suggest that not all of the ethanediolate ligands are displaced; therefore the completely cross-linked materials depicted in the foregoing equations represent idealized structures. The final composition of each sample depends on the vacuum distillation schedule employed. Ceramic yields of plastic and solid samples attain or surpass the theoretical yields for the idealized compositions.

Initial efforts to investigate the silicon environment of these materials by $^{29}Si$ NMR were thwarted by their high viscosity and the general reactivity of the diolate complexes with protic solvents. Model studies on the potassium polymer, II, reveal a shift from hexacoordinate geometry in the solid state ($^{29}Si$ MAS resonances at $-143.5$ and $-145.5$ ppm vs. TMS) to pentacoordination when the complex is dissolved in 1,2 ethanediol ($-108$ ppm). The lithium and potassium polymers, IA and IB, are pentacoordinate in either state. On this basis, it is concluded that the compounds represented by III, IV and V are anionic, pentacoordinate silicate oligomers.

The pentacoordinate nature of the Si in the polymer backbone of the invention is confirmed by the observation of a single $^{29}Si$ resonance at $-103$ ppm in polymer samples dissolved in dry $CDCl_3$. The corresponding $^{13}C$ spectra exhibit four $CH_2$ peaks shifted upfield by 0.6–0.8 ppm from those of $H_2PEO_4$, and a fifth peak at 77.2 ppm that is absent in $H_2PEO_4$. Upfield $^{13}C$ $CH_2$ shifts of 0.8 ppm in $Li^+$-doped PEO-co-siloxane polymers are correlated to cation oxygen interactions along the PEO chains. $^1H$ spectra on solid polymer samples dissolved in $CDCl_3$ show only traces of $-CH_2CH_2OH$.

The approximate composition of each material is determined from the corresponding char yield (Table 1) and the observation that tetraethylene glycol will coevaporate with 1,2-ethanediol during the final vacuum distillation. The following representative polymeric structures account for the observed ceramic yields, balance of charge, and pentacoordinate silicon geometry.

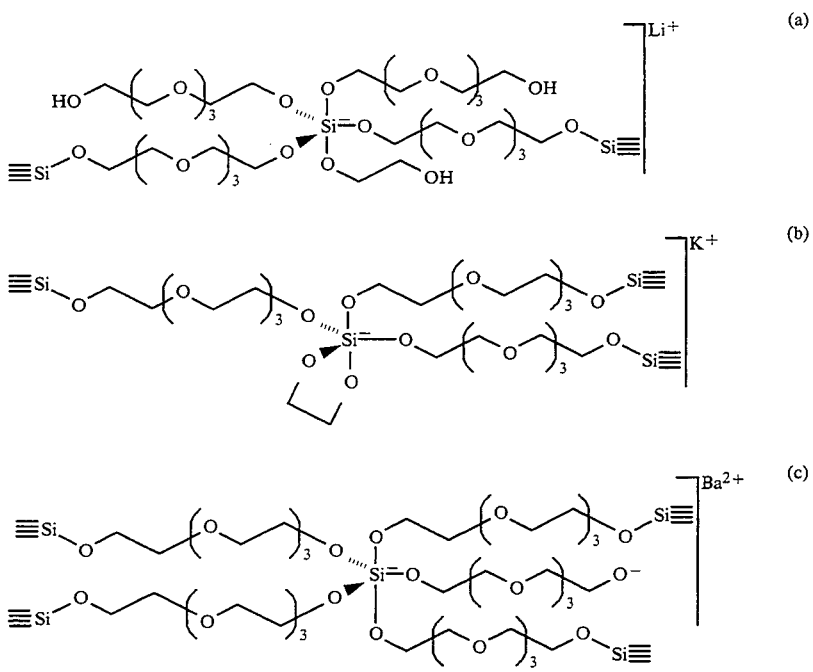

-continued

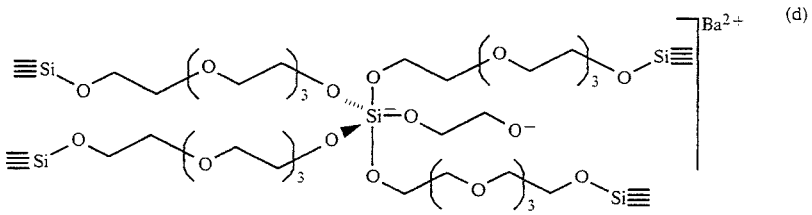

Other structures with different combinations of monodentate, bridging, and trapped neutral diols are possible. The theoretical (experimental) ceramic yields that correspond to the above structures are (a)$8.07\%$ (7.88%), (b)$25.8\%$ (24.5%), and (c) 28.8% (29.5%), and (d) 34.9% (33.4%).

The TGA of a rubbery sample of the barium polymer shows <2% mass loss below 175° C. Principal events occur at 200, 282, and 300 (sh)°C.; minor features appear at 313 and 359° C. In the lithium, potassium and barium precursors IA, IB, and II, above, the ethanediolate ligands are thermally stable to greater than or equal to 300° C. The TGAs of 1,2-ethanediol and $H_2PEO_4$ show complete mass loss at 125 and 196° C., respectively. However, PEO (MW $4 \times 10^6$) pyrolyzes in 4 steps at 253, 310, 337 (sh), and 459 (minor)°C. Mono-dentate —$(CH_2CH_2)_4OH$ or —$(OCH_2CH_2)_{40}$— ligands are expected to pyrolyze at somewhat higher temperatures than $H_2PEO_4$, whereas bridging $PEO_4$ should approximate the behavior of high MW PEO. Except for a broader first-step transition, the first derivative TGA curve of V from 200°–300° C. mimics the shape of the high MW PEO curve with a 30° C. shift to lower T. Although the 200° C. mass loss nearly coincides with the decomposition of $H_2PEO_4$, significant amounts of unreacted $H_2PEO_4$ in V were ruled out on the basis of $^1H$ NMR. Accordingly, dried samples of V lose the mono- and bi-dentate $PEO_4$ ligands between 200 and 300° C. The minor mass losses above 300° C. may result from decomposition of bound ethanediolate (if present) and, by analogy with the pyrolysis pattern of high ME PEO, fragments of $PEO_4$ chain. The thermograms of the lithium and potassium polymers, III and IV, show combustion patterns similar to that of the barium polymer V.

The lithium, potassium and barium tetra(ethylene oxide)silicate polymers, III, IV and V, undergo glass transitions at approximately $-25°$ C. (DSC), consistent with —$(OCH_2CH_2)$— links between silicon centers. Pure PEO exhibits a Tg at $-60°$ C. but $H_2PEO_4$ does not. $T_g$s between $-50$ and $-40°$ C. were reported for ion conducting crosslinked siloxane-ethylene oxide copolymers doped with $LiCF_3SO_3$. The higher $T_g$s in our ionic polymers likely result from the reduction of segmental motion under the influence of coulombic attraction and the shorter —$(OCH_2CH_2)$— links in $PEO_4$, relative to high molecular weight PEO.

The complex impedance measurements for viscous liquid samples of the lithium, potassium and barium tetra(ethylene oxide)silicate polymers III, IV, and V are also tabulated in Table 1, above. For comparison, solid state conductivities of $10^{-7}$ to $10^{-4}$ S cm$^{-1}$ have been obtained for Li-doped, silicate-intercalated PEO materials at elevated temperatures. Novel propylsiloxane ethyleneoxide copolymers that were doped with LiClO$_4$ exhibited solid state conductivities of $10^{-7}$ to $10^{-5}$ $\Omega^{-1}$cm$^{-1}$ at ambient temperature. The relatively high conductivity ($\kappa$) of the anionic $PEO_4$-silicates of the invention can be attributed to moderate viscosity and the ability of the $PEO_4$ chains to solubilize the cation. However, the presence of trapped glycol, suggested by the thermogravimetric compositional analysis (TGA), may also contribute to the observed conductivities.

The AC impedance plots of the lithium and barium polymers show typical semicircular plots. Surprisingly, the impedance of the potassium analog manifests a frequency-independent response except at very high frequency where a small $RC_p$ effect is observed, which is characteristic of pure electrolytes.

Conductivity is dependent on ion concentration and the factors that determine ion mobility: ionic radius, charge, and solution viscosity. On this basis, the expected relative conductivities of the three samples would be III>IV and V>IV. However, the low $\kappa$ of III suggests a stronger interaction of the anionic sites with the small Li cations than with either K$^+$ or Ba$^{2+}$. Likewise, Ba$^{2+}$ may be more tightly held in the polymer network than K$^+$, perhaps through simultaneous interaction of two anionic sites with the divalent cation. However, a two-fold factor between the $\kappa$ values for IV and V is not sufficient to warrant further speculation.

As described above, ionically conducting organosilicate polymers have been prepared in a simple one step process directly from $SiO_2$, 1,2-ethanediol, $H_2PEO_4$ and group I or II metal hydroxides or oxides, respectively. Alternatively, the ethanediolatosilicate intermediate can first be isolated and then reacted with $H_2PEO_4$ to synthesize the same polymers. These compounds have a $PEO_4$-pentacoordinate silicon backbone that remains amorphous at low temperatures, and are thermally stable from $-70$ to 200° C. Compositions depend on the vacuum distillation schedule and range from compounds containing mixtures of monodentate and bidentate ligands to fully cross-linked materials.

The invention now being fully described, it will be apparent to one of ordinary skill in the art that many changes and modifications can be made thereto, without departing from the spirit or scope of the invention as set forth herein.

The embodiments of the invention in which an exclusive property or privilege is claimed are defined as follows:

1. A polymer having the following general formula:

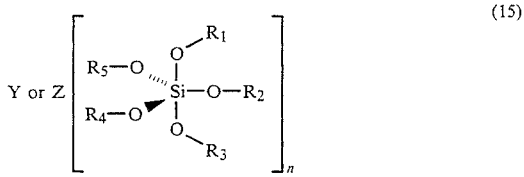

wherein $R_1$ through $R_5$ contain a carbon atom bonded directly to an oxygen atom of the above structure and are independently selected from the group consisting of

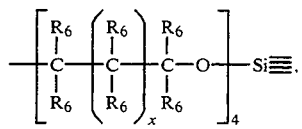

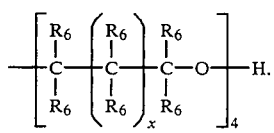

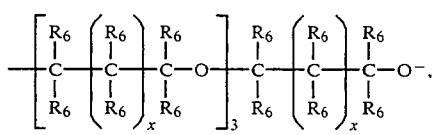

can be taken together to be —CH$_2$CH$_2$—, with the proviso that at least three of R$_1$ through R$_5$ must be,

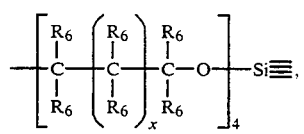

x is 0 or 1, each R$_6$ is independently selected from H, OH, C$_{1-6}$alkyl, O—C$_{1-6}$alkyl, C$_{2-6}$alkene, C$_{6-12}$aryl, C$_{1-6}$hydroxyalkyl, C$_{1-6}$thioalkyl, C$_{2-12}$alkoxyalkyl, C$_{3-20}$heteroaromatic, and combinations thereof, wherein each R group may also contain other, non-carbon elements such as Si, Sn, Ge, P, and the like; Y is monovalent cationic, Z is multivalent cationic, preferably dicationic and n is from 2 to 10,000.

2. A polymer according to claim 1, wherein each R$_6$ is independently a methyl group or H.

3. A polymer according to claim 1, wherein each R$_6$ is H.

4. A polymer according to claim 1, wherein Y is an alkali metal cation.

5. A polymer according to claim 1, wherein Z is an alkaline earth metal cation.

6. A polymer according to claim 1, wherein Y is Na$^+$, K$^+$, Li$^+$ or Cs$^+$.

7. A polymer according to claim 1, wherein Z is Mg$^{2+}$, Ca$^{2+}$, Ba$^{2+}$, Ni$^{2+}$ or Co$^{2+}$.

8. A silicon polymer selected from the group consisting of

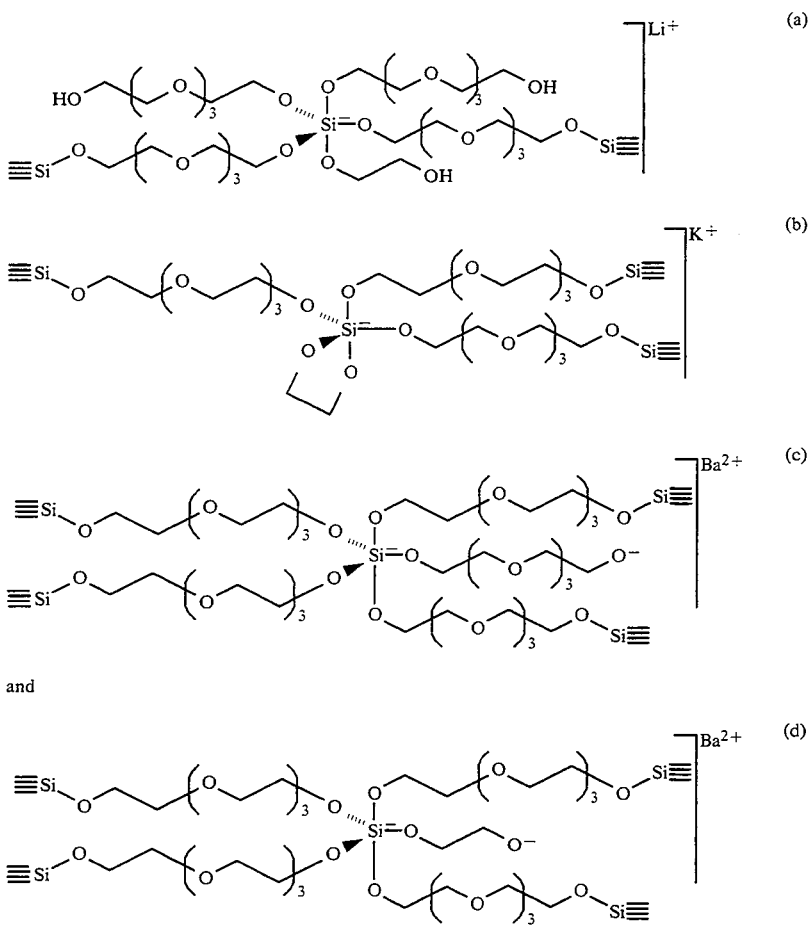

9. A method of producing a silicon polymer, which comprises: reacting silica with a compound having the formula:

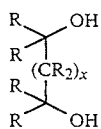

wherein x is 0 or 1; each R is independently selected from the group consisting of H, OH, $C_{1-6}$alkyl, $C_{1-6}$alkoxy, $C_{2-6}$alkene, $C_{6-12}$aryl, $C_{1-6}$hydroxyalkyl, $C_{1-6}$thioalkyl, $C_{2-12}$alkoxyalkyl, $C_{3-20}$heteroaromatic, and combinations thereof in the presence of a base and with removal of water formed during the reaction to produce an intermediate alkane(diolato)silicate salt, heating the alkane(diolato)silicate salt in the presence of a polyalkylene oxide in an inert atmosphere, and then subjecting the mixture to vacuum distillation at elevated temperatures to obtain the silicon polymer.

10. A method according to claim 9, wherein said reaction is conducted at a temperature of from about 20° C. to about 200° C.

11. A method according to claim 9, wherein said water is removed by distillation.

12. A method according to claim 11, wherein said water is removed by azeotropic distillation.

13. A method according to claim 9, wherein the polymer produced in said reaction is recovered by filtration followed by crystallization.

14. A method of claim 9, wherein said water is removed by reaction with water scavenger.

15. A method of claim 9, wherein said water is removed by membrane transport.

16. A method of claim 9, wherein said polymer has the formula:

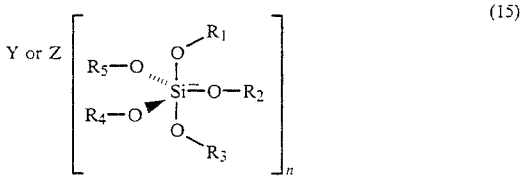
(15)

wherein $R_1$ through $R_5$ contain a carbon atom bonded directly to an oxygen atom of the above structure and are independently selected from the group consisting of

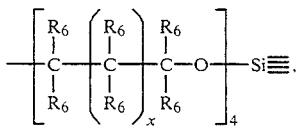

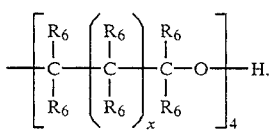

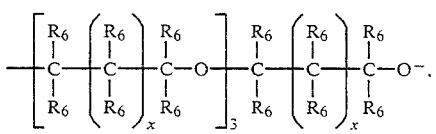

—$CH_2OH$ and —$CH_2O$—, or $R_3$ and $R_4$ can be taken together to be —$CH_2CH_2$—, with the proviso that at least three of $R_1$ through $R_5$ must be,

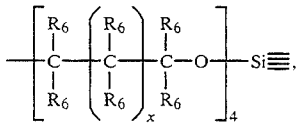

x is 0 or 1, each is independently selected from H, OH, $C_{1-6}$alkyl, O—$C_{1-4}$alkyl, $C_{2-6}$alkene, $C_{6-12}$aryl, $C_{1-6}$hydroxyalkyl, $C_{1-6}$thioalkyl, $C_{2-12}$alkoxyalkyl, $C_{3-20}$heteroaromatic, and combinations thereof, wherein each R group may also contain other, non-carbon elements such as Si, Sn, Ge, P, and the like; Y is monovalent cationic, Z is multivalent cationic and n is from 2 to 10,000.

* * * * *

UNITED STATES PATENT AND TRADEMARK OFFICE
CERTIFICATE OF CORRECTION

PATENT NO. : 5,440,011
DATED : August 8, 1995
INVENTOR(S) : R.M. Laine

It is certified that error appears in the above-indentified patent and that said Letters Patent is hereby corrected as shown below:

| COLUMN | LINE | |
|---|---|---|
| [56] | Refs. Cited (Other Publs.) | "O3 above in Herman" should read --O3 above in German-- |
| [56] | Refs. Cited (Other Publs.) | "USSR" should read --*USSR*-- |
| [56] | Refs. Cited (Other Publs.) | "Penta-alkoxy-and" should read --Penta-alkoxy- and-- |
| [56] | Refs. Cited (Other Publs.) (Bottom of page) | "(Abstract continued on next page.)" should read --(References continued on next page.)-- |
| [57] | Abstract (line 7 of text) | "sulicate" should read --silicate-- |
| [57] | Abstract (line 17 of text) | Before "can be taken" insert --$CH_2OH$ and -$CH_2O^-$, or R3 and R4-- |
| [57] | Abstract (line 18 of text) | "or" should read --of-- |

UNITED STATES PATENT AND TRADEMARK OFFICE
CERTIFICATE OF CORRECTION

PATENT NO. : 5,440,011  
DATED : August 8, 1995  
INVENTOR(S) : R.M. Laine

Page 2 of 10

It is certified that error appears in the above-indentified patent and that said Letters Patent is hereby corrected as shown below:

| COLUMN | LINE | |
|---|---|---|
| [57] | Abstract (line 20 of text) | "$R_6$is" should read --$R_6$ is-- |
| [57] | Abstract (line 23 of text) | "$C_{3-20}$heteraromatic" should read --$C_{3-20}$ heteroaromatic-- |
| [57] | Abstract (line 24 of text) | After "contain" insert --other,-- |
| [57] | Abstract (line 25 of text) | "monovalent Z" should read --monovalent cationic, Z-- |
| [57] | Abstract (line 26 of text) | "eationic" should read --cationic-- |
| 1 | 6 | After "abandoned" insert --,-- |
| 1 | 11 | After "U.S. Pat. No. 5,099,052." insert --The invention was made with government support under the following grants: N00014-88-K-0305 and F49620-89-C-0059. The government may have certain rights in this invention.-- |
| 2 | 50 | "non-reactivity" should read --nonreactivity-- |

UNITED STATES PATENT AND TRADEMARK OFFICE
CERTIFICATE OF CORRECTION

PATENT NO. : 5,440,011
DATED : August 8, 1995
INVENTOR(S) : R.M. Laine

It is certified that error appears in the above-indentified patent and that said Letters Patent is hereby corrected as shown below:

| COLUMN | LINE | |
|---|---|---|
| 3 | 10 | "$SiCl_4 + EtOH \rightarrow HCl + Si(OEt)_4$" should read --$SiCl_4 + EtOH \rightarrow 4HCl + Si(OEt)_4$-- |
| 4 | 15 | "penta-coordinate" should read --pentacoordinate-- |
| 4 | 17 | "Other publications" should begin a new paragraph. |
| 4 | 32 | "*J. Am. Chem. Soc.*93" should read --*J. Am. Chem. Soc.* 93-- |
| 4 | 64 & 65 | "$C_{2-1-2}$alkoxyalkyl" should read --$C_{2-12}$ alkoxyalkyl-- |
| 6 | 22 | Before "can be taken" insert --, $-CH_2OH$ and $-CH_2O^-$, or R3 and R4-- |
| 8 | 21 | "$C_{1-4}$alkyl" should read --$C_{1-4}$ alkyl-- |
| 8 | 23 | "OH'" should read --$OH^-$-- |
| 8 | 36 | "$Cl_6$hydroxyalkyl" should read --$C_{1-6}$ hydroxyalkyl-- |
| 8 | 38 | "(preferably 1-3 )" should read --(preferably 1-3)-- |
| 11 | 44 | "chains, $^{1,3,4}$" should read --chains. $^{1,3,4}$-- |
| 12 | 35 | "$-CH_2O-$" should read --$CH_2O^-$-- |

UNITED STATES PATENT AND TRADEMARK OFFICE
CERTIFICATE OF CORRECTION

PATENT NO. : 5,440,011
DATED : August 8, 1995
INVENTOR(S) : R.M. Laine

It is certified that error appears in the above-indentified patent and that said Letters Patent is hereby corrected as shown below:

| COLUMN | LINE | |
|---|---|---|
| 12 (structure (a)) | 61 | 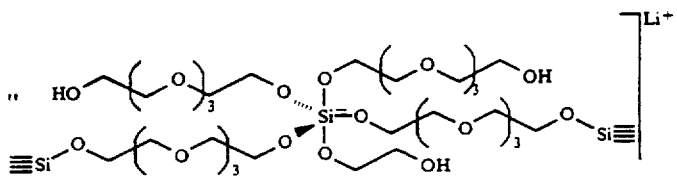 | should read

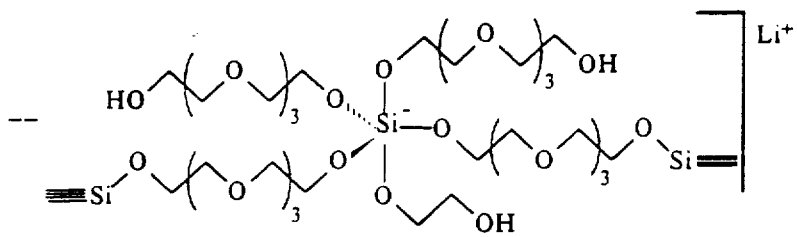  (a)

| 13 | 31 | "29Si" should read --$^{29}$Si-- |
| 13 | 68 | Unindent "A. General" |
| 14-18 | Begin at 29 | Indent paragraphs numbered "1-14" five spaces. |
| 14 | 49 | "Mg/MgI$_2$" should read --Mg/MgI$_2$-- |
| 14 | 64 | "flitrate" should read --filtrate-- |

UNITED STATES PATENT AND TRADEMARK OFFICE
CERTIFICATE OF CORRECTION

PATENT NO. : 5,440,011
DATED : August 8, 1995
INVENTOR(S) : R.M. Laine

It is certified that error appears in the above-indentified patent and that said Letters Patent is hereby corrected as shown below:

| COLUMN | LINE | |
|---|---|---|
| 15 | 10 | "$K_2Si_2(OCH_2CH_2O)_5$" should read --$K_2Si_2(OCH_2CH_2O)_5$-- |
| 17 | 36 | "$\{M[Si(PEO_4)_{2.5}]\}n$" should read --$\{M[Si(PEO_4)_{2.5}]\}_n$-- |
| 18 | 23 | "$10^5$" should read --$10^{-5}$-- |
| 18 | 30 | After "distilled off" insert --.-- |
| 19 | 1 | "calorimet" should read --calorimetry-- |
| 19 | 10 | "reposed" should read --reported-- |
| 19 | 10 | "5%/ST plots" should read --δ%/δT plots-- |
| 19 | 15 | "ns" should read --runs-- |
| 19 (TABLE 1) | 32 | "Li+" should read --$Li^+$-- |
| 19 (TABLE 1) | 33 | "K+" should read --$K^+$-- |

UNITED STATES PATENT AND TRADEMARK OFFICE
CERTIFICATE OF CORRECTION

PATENT NO. : 5,440,011
DATED : August 8, 1995
INVENTOR(S) : R.M. Laine

It is certified that error appears in the above-indentified patent and that said Letters Patent is hereby corrected as shown below:

| COLUMN | LINE | |
|---|---|---|
| 20 (structure (a)) | 43 | " 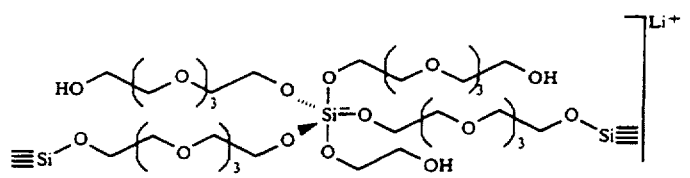 " | should read

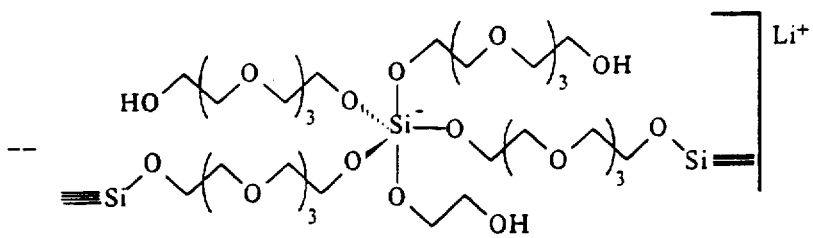

-- (a)

| | | |
|---|---|---|
| 21 | 14 | "(a)$_{8.07}$%" should read --(a) 8.07%-- |
| 21 | 15 | "(b)$_{25.8}$%" should read --(b) 25.8%-- |
| 21 | 27 | "-(OCH2CH2)4O-" should read ---(OCH2CH2)4O--- |
| 21 | 38 | "PEO4ligands" should read --PEO4 ligands-- |

UNITED STATES PATENT AND TRADEMARK OFFICE
CERTIFICATE OF CORRECTION

PATENT NO. : 5,440,011
DATED : August 8, 1995
INVENTOR(S) : R.M. Laine

It is certified that error appears in the above-indentified patent and that said Letters Patent is hereby corrected as shown below:

| COLUMN | LINE | | |
|---|---|---|---|
| 22 (Claim 1, formula (15)) | 60-65 | " 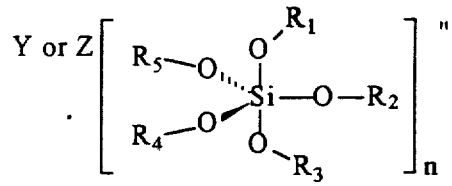 " should read 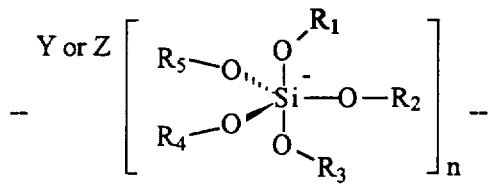 | |
| 23 (Claim 1) | 22 | Before "can be taken together" insert ---$CH_2OH$ and -$CH_2O^-$, or R3 and R4-- | |
| 24 (Claim 1, last line) | 7 & 8 | After "multivalent cationic" delete --, preferably dicationic-- | |

UNITED STATES PATENT AND TRADEMARK OFFICE
CERTIFICATE OF CORRECTION

PATENT NO. : 5,440,011
DATED : August 8, 1995
INVENTOR(S) : R.M. Laine

Page 8 of 10

It is certified that error appears in the above-indentified patent and that said Letters Patent is hereby corrected as shown below:

COLUMN          LINE 24                25
(Claim 8, line 3)
(structure (a))

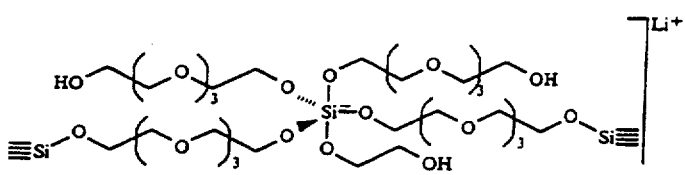
(a)

should read

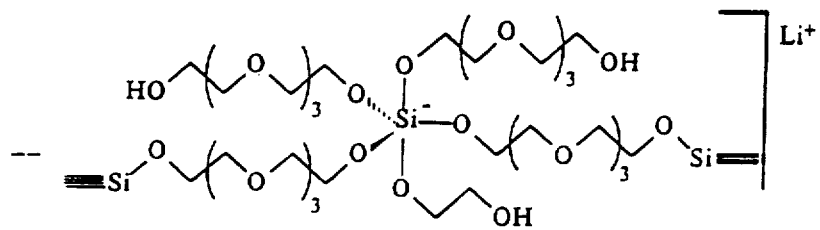

(a)

UNITED STATES PATENT AND TRADEMARK OFFICE
CERTIFICATE OF CORRECTION

PATENT NO. : 5,440,011
DATED : August 8, 1995
INVENTOR(S) : R.M. Laine

It is certified that error appears in the above-indentified patent and that said Letters Patent is hereby corrected as shown below:

COLUMN      LINE

| COLUMN | LINE | |
|---|---|---|
| 26 (Claim 16) | 10 | "$R_l$" should read --$R_1$-- |
| 26 (Claim 16) | 33 | "-$CH_2O$-" should read --$CH_2O^-$-- |

UNITED STATES PATENT AND TRADEMARK OFFICE
CERTIFICATE OF CORRECTION

PATENT NO. : 5,440,011
DATED : August 8, 1995
INVENTOR(S) : R.M. Laine

It is certified that error appears in the above-indentified patent and that said Letters Patent is hereby corrected as shown below:

| COLUMN | LINE | |
|---|---|---|
| 26 (Claim 16) | 44 | After "each" insert --$R_6$-- |
| 26 (Claim 16) | 45 | "O-$C_{1-4}$alkyl" should read --O-$C_{1-6}$ alkyl-- |

Signed and Sealed this

Thirtieth Day of January, 1996

BRUCE LEHMAN

Attest:

Attesting Officer

Commissioner of Patents and Trademarks